United States Patent [19]

Langhorst et al.

[11] Patent Number: 5,183,604
[45] Date of Patent: Feb. 2, 1993

[54] SIZE SEPARATION OF PARTICLES CONTAINED WITHIN A MATERIAL BY THE USE OF NONAQUEOUS HYDRODYNAMIC CHROMATOGRAPHY

[75] Inventors: Martin A. Langhorst, Midland, Mich.; Joseph B. Henry, Pickerington, Ohio

[73] Assignee: The Dow Chemical Company, Midland, Mich.

[21] Appl. No.: 825,353

[22] Filed: Jan. 24, 1992

[51] Int. Cl.⁵ .................. B29C 45/00; B01D 15/08
[52] U.S. Cl. .............................. 264/40.1; 264/236; 264/347; 210/656; 210/659; 210/198.2; 209/1; 209/155; 209/209
[58] Field of Search ............. 264/40.1, 236, 347; 210/635, 656, 198.2; 209/1, 155, 209

[56] References Cited

U.S. PATENT DOCUMENTS

| | | | |
|---|---|---|---|
| 2,379,158 | 6/1945 | Kalischer | 88/14 |
| 3,389,334 | 6/1968 | Coulter et al. | 324/71 |
| 3,519,353 | 7/1970 | Franz et al. | 356/102 |
| 3,865,717 | 2/1975 | Small | 201/1 |
| 3,890,046 | 6/1975 | Hart et al. | 356/37 |
| 4,001,595 | 1/1977 | Reisman | 250/575 |
| 4,510,438 | 4/1985 | Auer | 324/71.4 |
| 4,532,043 | 7/1985 | Prud'homme et al. | 210/635 |
| 4,629,566 | 7/1985 | Prud'homme et al. | 110/635 |
| 5,089,126 | 2/1992 | Silebi | 210/656 |

Primary Examiner—Ernest G. Therkorn
Attorney, Agent, or Firm—James T. Hoppe; Burke M. Halldorson

[57] ABSTRACT

A method is disclosed for determining the distribution according to size of particles which make up a noncontinuous phase dispersed within a matrix which is not completely soluble in an aqueous solution. The method involves dissolving the matrix containing the particles in an essentially nonaqueous liquid causing the particles to be suspended. The suspension is then eluted through a separating medium which sorts the particles according to size. A detector monitors the effluent from the separating medium and creates a record of the data. This record is then compared to data obtained from known standards in order to estimate the size distribution in the sample.

14 Claims, 2 Drawing Sheets

SIZE SEPARATION OF PARTICLES CONTAINED WITHIN A MATERIAL BY THE USE OF NONAQUEOUS HYDRODYNAMIC CHROMATOGRAPHY

FIELD OF THE INVENTION

This invention relates to a method for the separation by size of particles contained within a matrix and more particularly to the use of nonaqueous hydrodynamic chromatography to separate these particles and to provide data which is indicative of the size distribution of these particles within the matrix.

DESCRIPTION OF THE PRIOR ART

There are many applications which require the placement of particles within a matrix in order to modify the physical properties of the given matrix. For example, rubber particles are commonly dispersed within a polymer matrix in order to alter the physical properties of the polymer. The number and the size of the particles contained in the matrix significantly influences the type and the level of the physical modification that is accomplished. Therefore, it is highly desirable to determine the distribution according to size of these particles within the matrix. Once the distribution according to size of the particles is known, the general physical characteristics of the material as a whole can be accurately estimated.

There are many techniques for measuring such particle size distributions. For instance, it is known that a Coulter counter may be used to accurately determine the particle size distribution, when the contained particles have diameters greater than approximately 0.5 micrometers. While the Coulter counter is effective, the size distribution produced by the Coulter counter will be highly inaccurate if some or all of the dispersed particles have diameters which are less than 0.5 micrometers. Therefore, the Coulter counter is not useful for all applications.

Another method which may be used to determine the dispersed particle size distribution involves the use of a transmission electron microscope. While the transmission electron microscope does allow for the accurate determination of the particle size distribution, it is relatively costly and is inefficient since a relatively great amount of time and effort is required to prepare the sample for analysis and to measure the output from the transmission electron microscope.

Still another method which may be used to characterize the size distribution of particles dispersed within a matrix utilizes hydrodynamic chromatography which is generally described in U.S. Pat. No. 3,865,717 to Small. The use of such hydrodynamic chromatography in the characterization of molecular weight distribution is described in U.S. Pat. Nos. 4,532,043 and 4,629,566 to Prudhomme and Langhorst. U.S. Pat. Nos. 3,865,717, 4,532,043 and 4,629,566 are all incorporated herein by reference.

The current practice of hydrodynamic chromatography is limited, however, in that the technique has only been developed for use with aqueous solutions. Accordingly, the matrix containing the dispersed particles must be completely soluble in an aqueous solution for the current hydrodynamic chromatography methods to be effective. Matrices which are not completely soluble in aqueous solutions can not be analyzed by the existing hydrodynamic chromatography techniques, as the detector will not be able to distinguish between the particles dispersed in the matrix and the clumps of undissolved matrix. This severely limits the usefulness of the technique as there are many potential applications where particles are dispersed in matrices such as thermoplastics and thermosets, which are not completely soluble in aqueous solutions.

SUMMARY OF INVENTION

It is therefore a primary object of the invention to provide a method for separating particles according to size, where the particles are contained within a matrix which is not completely soluble in an aqueous solution. A further object of this invention is to provide a relatively efficient and cost effective method for the generation of data which may be used to determine the size distribution of particles contained within a non-water-soluble matrix. It should mbe understood that "distribution" refers to both the range of particle sizes and the concentration of each particle size.

According to one aspect of this invention, a method is provided for determining the distribution according to size of particles contained within a matrix. This method comprises the steps of dissolving the matrix in a solvent leaving the previously contained particles dispersed in the solvent/matrix mixture; adding the particles and the mixture to a nonaqueous carrier liquid; eluting the particles through a separation medium effective for sorting the particles as a function of size wherein increasingly smaller particles are eluted at increasingly later times; and detecting the concentration of the eluted particles with respect to time.

According to another aspect of this invention, an improved method for producing materials comprising a continuous phase which is not completely soluble in aqueous solutions and a non continuous phase is provided. Presently, the known method of producing such materials involves determining the size distribution of the particles to be dispersed, and then once the distribution has been established to be acceptable, adding the particles to the polymerization process. Thus, any changes in the morphology of the particles which might occur during the later processing steps, are not taken into account. Therefore, the present invention provides a way of analyzing the product at later stages of the process, so that a more accurate determination of the particle size distribution can be made. This in turn leads to greater control over the reaction and less generated waste.

Further objects, features, and advantages of the invention will become apparent from the consideration of the following description and the appended claims when taken in conjunction with the accompanying drawings.

DETAILED DESCRIPTION OF THE INVENTION

I. Overview of Nonaqueous Hydrodynamic Chromatography of this Invention

Figure 1:
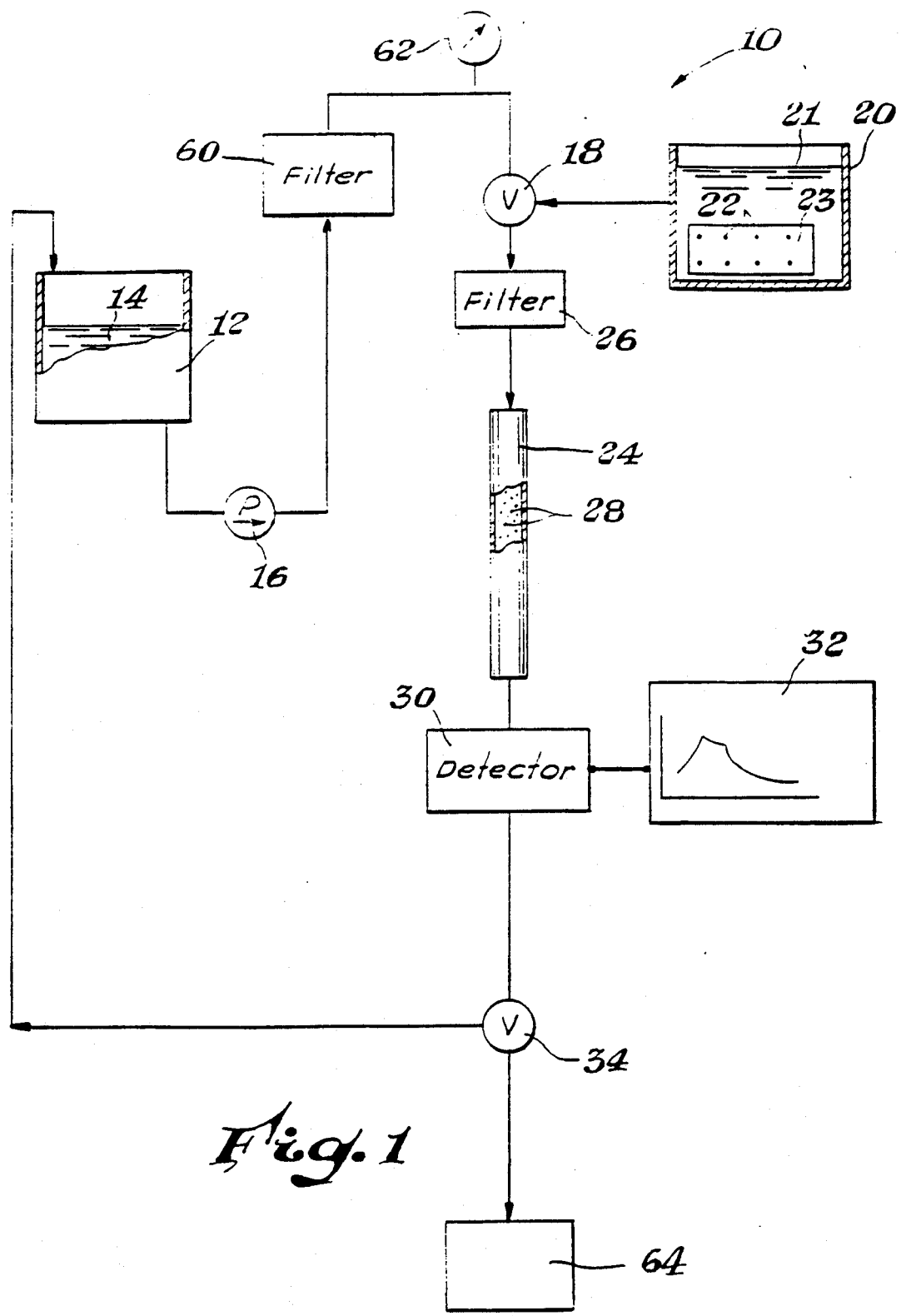
FIG. 1, is a block diagram of a nonaqueous chromatographic apparatus of the preferred embodiment for practicing the method of this invention.

Referring now to FIG. 1 there is shown a preferred embodiment of a chromatographic apparatus 10, which is suitable for practicing this invention. The chromatographic apparatus 10 is shown to include a nonaqueous carrier eluant reservoir 12 containing a nonaqueous carrier liquid 14. The carrier liquid 14 is pumped by pump 16 through a filter 60 which, in the preferred embodiment of the invention, has a nominal porosity of approximately 0.1 micrometers. The carrier liquid then flows past a pressure gauge 62 to input valve 18. The input valve 18 allows an aliquot of sample to be admitted to the chromatographic system 10. The carrier liquid 14 contacts the sample at input valve 18 and continues to mix with the sample as it sweeps the sample to a separating medium 24.

FIG. 1 also shows a second reservoir 20 containing a nonaqueous solvent 21. The sample to be analyzed is added to this solvent 21. The sample to be analyzed comprises a matrix 23 containing a distribution of particles 22. The matrix 23 can be comprised of any material capable of forming a continuous phase which is soluble in a nonaqueous solvent 21. Nonaqueous hydrodynamic chromatography is most often used with samples whose matrices are of a relatively high molecular weight such as thermoplastics and thermosets, as these molecules tend to be the least soluble in solutions containing water, and therefore the least likely to be analyzable by traditional hydrodynamic chromatography. In a preferred embodiment of this invention the matrix 23 is comprised of polystyrene or poly(styrene-acrylonitrile). The particles 22 can be comprised of any material which is insoluble in the chosen nonaqueous solvent 21 and is capable of being separated from the supporting matrix 23. In a preferred embodiment of the invention the particles are comprised of polybutadiene. Accordingly, when the sample to be analyzed is added to the nonaqueous solvent 21, the matrix is dissolved leaving the previously contained particles dispersed in a solution of the solvent 21 and the dissolved matrix 23. The concentration of sample in the solvent 21 must be adjusted so that the output stays within the linear range of the detector 30. In one particular application, the concentration of the resulting suspension was approximately 3-4 mg of dissolved matrix 23 and approximately 1 mg of suspended particles 22 per mL of the nonaqueous solvent 21.

In a preferred embodiment of this invention, a dimension fixing agent such as osmium tetroxide is added to the solvent 21. Dimension fixing agents act to stabilize the morphology of particles which otherwise might be altered when exposed to different fluids. Accordingly, by adding the dimension fixing agent to the solvent 21, the particles 22 are contacted with the dimension fixing agent immediately after being exposed, thereby stabilizing the morphology of the particles before any changes occur.

Additionally, in a preferred embodiment of this invention, a marker solution is added to the solvent 21 containing the suspended particles 22 and dissolved matrix 23. This marker solution identifies any variances in the flow rate of the apparatus, allowing the analyst to compensate for any changes when calculating the size distribution of a particular sample. The marker solution must be compatible with the carrier liquid 14 and the solvent 21, and be responsive to the detection means chosen. Furthermore, the marker should elute from the column at a time such that it does not interfere with the elution of the distribution of particles 22. In the preferred embodiment of this invention the marker selected was 0-dinitrobenzene.

Approximately 20-25 microliters of the mixture containing the sample to be analyzed is admitted to the apparatus 10 via the input valve 18 which is typically an injection valve for use with a syringe or similar device. Once admitted to the apparatus 10, the matrix 23/solvent 21 solution and the suspended particles 22 are mixed with the flowing carrier liquid 14. The carrier liquid 14 then directs the material through a second filter 26 and then to a separating medium 24. In the preferred embodiment of the invention, the second filter 26 has a nominal porosity of approximately two micrometers, and the separating medium 24 is a commercially obtained chromatography column filled with a packing material 28 which is more completely described below. The column preferably has a length of approximately 30 centimeters and an inside diameter of approximately 7.5 millimeters.

As the mixture from valve 18 flows through the separating medium 24, the separating medium acts to sort the particles 22 by size. In the preferred embodiment, the particles 22 will exit the column in order of decreasing size. In other words, the particles having the largest diameters will exit the column 24 first, followed by the particles having the smallest diameters, and finally the dissolved matrix 23 and the marker.

Once the particles 22 elute from the separating medium 24, they are detected by the detector 30 which produces a chromatogram 32 or similar set of data which indicates the distribution according to size of the particles 22 within the matrix 23. In the preferred embodiment of this invention, detector 30 is a turbidity detector such as a Kratos Model 773 Ultraviolet variable wavelength detector. After passing through the detector 30, the carrier liquid 14 enters a switching valve 34 and, depending on whether or not the carrier fluid 14 contains any of the sample, is directed either to waste 64 or back to reservoir 14 for use in a future analysis.

The chromatogram 32 produced by the detector 30 may be analyzed in a number of ways, in order to acquire a substantially accurate measure of the size distribution of particles 22 within the dissolved material 23. One example of such possible analysis is explained within the article entitled "Development and Application of an Integrated High-Speed Computerized Hydrodynamic Chromatograph." written by G. McGowan and M. Langhorst, J. Coll. Int. Sci. 89, 94 (1982).

Additionally, in the preferred embodiment of this invention, the column 24 is calibrated using four different standards which contain particles having diameters substantially equal to 1100, 2500, 4000, and 5000 Angstroms, respectively. It is important to choose particle standards which are compatible with the nonaqueous carrier fluid. This means that the change in size of the particles when suspended in the fluid must be known, or more preferably, the particles in the standard should not be altered at all by the carrier fluid. Microscopy, light scattering or some other known technique can be used to detect any changes in the morphology of the particles in the standard when exposed to the nonaqueous liquid.

In the preferred embodiment of this invention, the chosen standards are polybutadiene mixtures. These polybutadiene standards are substantially similar to those used in the calibration of hydrodynamic chromatography using aqueous liquids. The standards are first suspended in an aqueous solution containing a surfactant, such as Brij-35 ™, and then added to a solution of dimethylformamide (DMF) and a marker solution of 0-dinitrobenzene. The surfactant acts to preserve the monodispersion of the particles in the suspension as it changes from an aqueous based suspension to an essentially nonaqueous suspension. The standard solutions were then admitted to the system via input valve 18. The detector response was closely monitored and recorded as the standards eluted from the column 28. The calibration technique using the recorded results from these standards was thereafter substantially similar to the calibration technique used in hydrodynamic chromatography employing aqueous liquids.

II. Column Packing

The packing material 28 (FIG. 1), which fills the separating medium 24 in the preferred embodiment of this invention, is selected such that it remains stable and does not chemically react with the nonaqueous liquids 14 and 21. Additionally, the particles which comprise the packing material 28 must be impermeable to the suspended particles 22 that are being analyzed. Impermeability can be achieved by using essentially nonporous particles for the packing material 28. Highly cross-linked poly(styrene-divinyl benzene) is relatively unreactive, will remain stable when placed in contact with most nonaqueous liquids which may be used as the carrier liquid 14 or the solvent 21, and is essentially nonporous. Furthermore, it has been observed that when the packing material 28 is comprised of highly cross-linked poly(styrene-divinyl benzene) the column can successfully fractionate particles 22 which have diameters ranging from about 0.1 to 1 micrometer. Therefore, in the preferred embodiment of this invention, the packing material 28 in the separating medium 24 is comprised of poly(styrene-divinyl benzene).

The size of the individual components of the packing material 28 is also important. Using smaller sized components will increase the resolution of the suspended particles 22, but will also increase the likelihood of trapping some of the particles in the separating medium 24. Trapping appears to occur when the suspended particles 22 enter a region of quiescent fluid. The number of these quiescent regions increases with decreasing diameters of the packing material 28. Larger particles tend to get trapped in these quiescent regions more readily than smaller particles, perhaps due to decreased levels of Brownian motion. Trapped particles do not elute from the column and consequently are not detected by the detector 30. This produces a misleading analysis as the resulting chromatogram 32 reflects only the contained particles 22 which were small enough to elute from the separating medium, rather than the true distribution of all of the contained particles 22 (i.e., the trapped particles 22 are not included within the produced chromatogram 32). Therefore, the packing material 28 used to fill the chromatography column in the preferred embodiment of the invention, should be of small enough size to effectively sort the suspended particles 22, yet large enough to ensure that virtually none of the particles 22 are trapped.

Experience has shown that for particle distributions in which some of the particles 22 have diameters greater than approximately 0.5 micrometers, the diameter of individual components of the packing material 28 should be approximately 20 micrometers in order to prevent trapping of the particles 22. Alternatively, if the diameters of substantially all of the suspended particles 22 are smaller than approximately 0.5 micrometers, then the components of the packing material should have diameters of approximately 10 micrometers in order to maximize the resolution of the various sized particles.

III. Choice of Nonaqueous Liquid

In selecting the essentially nonaqueous liquids to be used for the carrier liquid 14 (FIG. 1) and the solvent 21 several factors must be considered. First of all, the continuous phase matrix 23 must be completely soluble in the solvent 21. Thus, small amounts of water may be present in the nonaqueous liquid, as long as the continuous phase matrix 23 can be completely dissolved. The upper limit of water concentration in the essentially nonaqueous liquids is determined by the solubility of the particular sample being analyzed.

Secondly, the carrier liquid 14 must be compatible with the solvent 21 and the dissolved matrix 23 so that a stable suspension of the particles 22 may be formed. For the purposes of this invention, the test for determining if a stable suspension has been formed consists of three parts. First, the matrix 23 must remain dissolved. Secondly, the morphology of the particles 22 must not have been significantly altered when forming the suspension. Finally, the particles 22 must be able to be uniformly dispersed in the solution to ensure that a representative sample can be taken. These three requirements must be satisfied for there to be a stable suspension. Accordingly, the carrier liquid 14 and the solvent 21 should be carefully chosen to achieve these goals.

Additionally, the viscosity of the carrier liquid 14 must be such that it can be delivered by conventional pumping means without excessive heating. Finally, the nonaqueous liquids 14 and 21 should be chosen so as not to interfere with the detector (e.g. if the detector is based on the particles absorbing light at a particular wavelength, then the liquids 14 and 21 should not strongly absorb light at that wavelength.)

Many possible nonaqueous liquids 21 may be used to dissolve the matrix material (i.e. polystyrene or poly(styrene-acrylonitrile)) containing the particles 22. Examples of such liquids include toluene, methyl ethyl ketone, and tetrahydrofuran. These liquids, while capable of dissolving the continuous solid phase material have been found to alter the size and/or the morphology of the contained particles 22, typically by swelling them. The alteration of the particles 22 results in an incorrect analysis of the size distribution. For example, a small particle, which is made to swell by the solvent 21, will elute from the separating medium 24 faster than would otherwise be expected. Consequently, the analyst will infer that the particle has a larger size than its actual size when dispersed in the matrix 23. Thus, it can be seen that swelling or any other other modification of the particles 22, results in an incorrect chromatogram 32 which leads to a misleading analysis.

Dimethylformamide (DMF), on the other hand, adequately dissolves polystyrene and poly(styrene-acrylonitrile) without substantially swelling the dispersed particles 22. Furthermore, DMF creates a stable suspension, and does not interfere with the UV turbidity detector in the preferred embodiment of this invention. For these reasons, dimethylformamide is used in the preferred method of this invention. Furthermore, in the preferred embodiment of the invention DMF comprises both the solvent 21 and the carrier liquid 14, thereby simplifying the operation and avoiding any miscibility problems.

EXAMPLE I

Separating Particles Contained Within a Material and Producing Data Which is Indicative of the Distribution of the Particles The apparatus and general methodology utilized in this and all of the Examples was substantially similar to that fully described above. Initially, a sample of a polymer was obtained which defined a continuous solid phase of polystyrene and a discontinuous solid phase defined by a distribution of rubber particles. Approximately 10 milliliters of dimethylformamide was delivered at room temperature to approximately 100 mg of this obtained polymer. After a time, it was observed that the continuous solid phase material was dissolved and that the rubber particles were freely suspended within the delivered dimethylformamide. Thereafter, the suspended rubber particles and the dimethylformamide were sonicated for approximately sixty seconds. After sonication, approximately 10 milliliters of a nonaqueous liquid carrier medium, substantially comprising dimethylformamide and approximately 200 microliters of a liquid marker solution, was added to the existing dimethylformamide and rubber particle suspension. The marker solution was prepared by dissolving O-dinitrobenezene in dimethylformamide such that the concentration of the marker solution was approximately 10 mg of O-dinitrobenezene per mL of dimethylformamide.

Thereafter, approximately 20-25 microliters of the suspension was injected through valve 18. The suspended rubber particles were eluted through column 24 by the carrier fluid 14 which was flowing at a rate of approximately 1 mL per minute. The particles eluted from the column in descending order of diameter size and were detected by the turbidity detector 30, operating at a wavelength of approximately 280 manometers.

The resulting chromatogram 32 was indicative of the distribution according to size of the rubber particles within the sampled polymer. This chromatogram was analyzed in a manner described by McGowan and Langhorst in *J. Coll. Int. Sci.*, 89, 94 (1982) and the size distribution of the rubber particles within the sample polymer was calculated. This calculated size distribution was compared to the results obtained from a transmission electron microscope. The comparison indicated that the analysis performed using nonaqueous chromatography according to the preferred embodiment of this invention was substantially similar to the analysis performed using a transmission electron microscope. Thus, analyses performed using nonaqueous hydrodynamic chromatography are comparable to analyses performed using a transmission electron microscope, but the results are obtained faster and at a lower cost than when using the transmission electron microscope.

EXAMPLE II

Addition of Osmium Tetroxide to the Nonaqueous Solvent

It has been determined, as discussed above, that dimethylformamide will dissolve the solid continuous phase material 23, without appreciably swelling the particles 22. However, it has also been observed that these particles 22 may contain occlusions which may cause the particles 22 to actually decrease in size as the nonaqueous solvent 21 dissolves the continuous solid phase material 23 and comes into contact with the particles 22. Consequently, in order to minimize any changes in size of the particles 22, dimension fixing agents can be added. Several dimension fixing agents are known and described in the literature. One of these, osmium tetroxide ($OsO_4$), was chosen to be evaluated.

To assess how effective osmium tetroxide is at stabilizing the morphology of particles 22, the following experiment was performed. Samples of mass polymerized acrylonitrile-butadiene-styrene (ABS) terpolymer and high gloss high impact polystyrene were prepared in typical fashion, such that each sample was comprised of a matrix material, and a discontinuous solid phase consisting of rubber particles. The high gloss high impact polystyrene polymer was specifically made to contain a capsule rubber particle morphology. Both of the prepared polymers were then individually placed into similar solutions. These solutions were prepared by adding approximately 50 microliters of a 3% $OsO_4$ in water solution to approximately 10 mL of dimethylformamide.

The dimethylformamide was observed to dissolve both of the matrix materials, resulting in a suspension of the previously contained rubber particles. As the matrix materials dissolved, the surfaces of the suspended rubber particles became exposed and were stained by the osmium tetroxide. After both of the matrix materials were substantially dissolved and the contained rubber particles were suspended in the solutions of dimethylformamide and osmium tetroxide, the two solutions were centrifuged at a speed of approximately 14,000 rotations per minute (rpm). The supernatant dimethylformamide containing the dissolved matrix material was decanted and replaced with fresh dimethylformamide in each sample.

The two solutions containing the fresh dimethylformamide and the suspended rubber particles from each of the original samples, were then centrifuged again at a speed of approximately 14,000 rotations per minute. The supernatant dimethylformamide was decanted leaving the rubber particles. The resultant rubber particles were then mixed with glue, allowed to harden, stained, thin-sectioned, and then imaged with a transmission electron microscope. The images of the rubber particles obtained from the electron microscope confirmed that the osmium tetroxide substantially prevented any change to the morphological structure of the rubber particles in both samples.

EXAMPLE III

Use of Nonaqueous Hydrodynamic Chromatography in Pre-Polymer Applications

Figure 2:
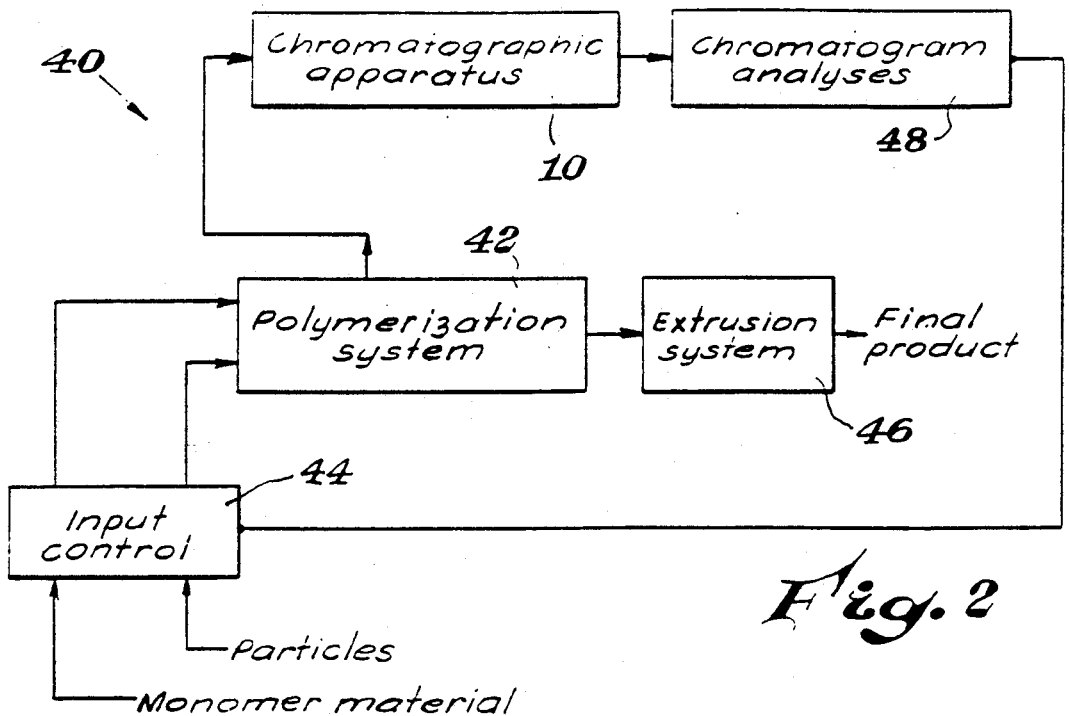
FIG. 2, is a block diagram illustrating the use of the method of the preferred embodiment of this invention within a polymerization process.

The methodology and apparatus, previously discussed, associated with nonaqueous hydrodynamic chromatography of the preferred embodiment of this invention, may also be used to determine the distribution of particles 22 contained within a partially polymerized material. This allows greater control in a reinforced polymer production process. One such application in this regard is shown in FIG. 2 which depicts a typical polymerization process 40. Specifically, in a typical polymerization process 40 a quantity of a monomer material and a quantity of rubber particles are fed into a polymerization system 42 through an input control system 44. The input control system 44 controls the quantities of monomer and rubber particles entering the system 42. In one embodiment the input control system 44 comprises a pair of flow control valves. The polymerization system 42 distributes the particles into the monomer, polymerizes the monomer, and then delivers the resultant polymerized material to a typical extrusion system 46, which produces a final extruded polymer product containing reinforcing rubber particles.

A sample of the partially polymerized liquid of system 42 can be drawn off and analyzed using the apparatus 10 shown in FIG. 1 and the previously discussed methodology of this invention. Thus, a chromatogram indicating the distribution according to size of the rubber particles can quickly be produced. The chromatogram can then be evaluated by the analysis system 48 to determined the range of particle sizes in the partially polymerized sample, as well as the concentration of each size particle. Upon this determination, the analysis system 48 signals the input control system 44 in order to adjust the flow of rubber particles into the polymerization system 42 to correct for any deficiencies or overabundance of the particles in the polymerization system 42. Furthermore, if the range of particle sizes is unacceptable, the analysis system 48 can shut the system down and notify the operator of faulty rubber particle feedstock. In this way, the quality and composition of the final product produced by the system is held at a substantially consistent level, thereby reducing waste.

EXAMPLE IV

Use of Nonaqueous Hydrodynamic Chromatography in a Blending Application

Figure 3:
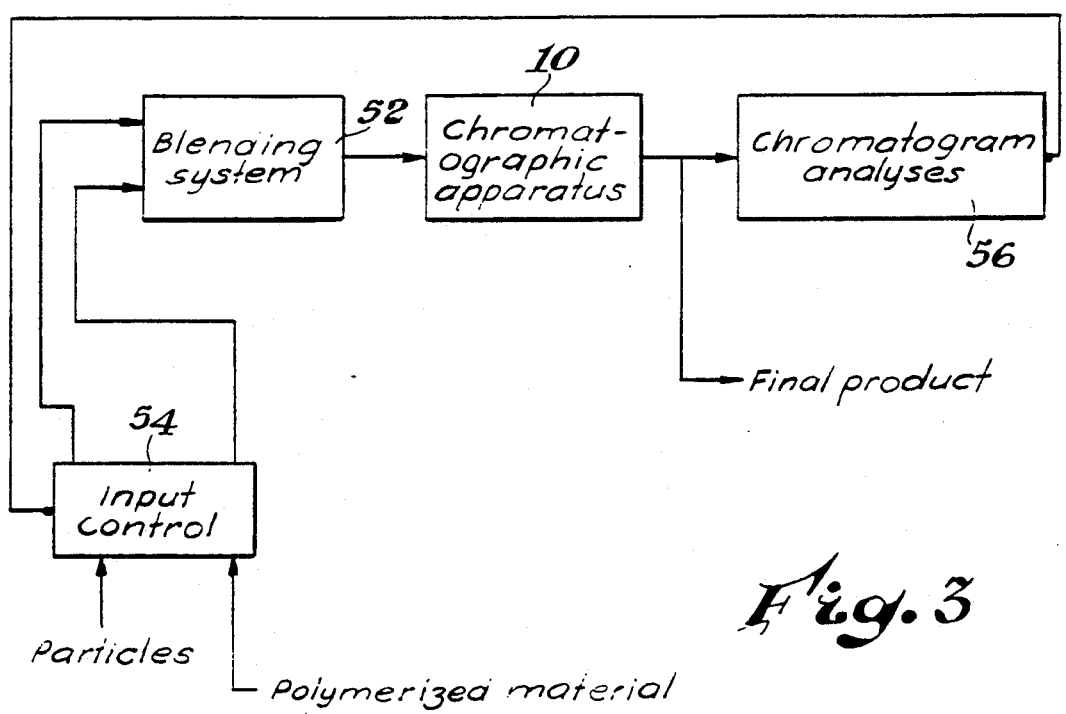
FIG. 3 is a block diagram illustrating the use of the method of the preferred embodiment of this invention with a blending process.

Referring to FIG. 3, there is shown a typical blending process 50. In a typical blending process, a polymerized material and a quantity of rubber particles are fed into a typical blending system 52, through an input control system 54 (i.e., a pair of flow control valves). The system 52 blends the particles and polymerized material together producing a final product therefrom. The quality of the final product is usually dependent on the distribution of the rubber particles that in contains.

As in Example III, waste can be reduced by regularly sampling and analyzing the final product using the apparatus 10 pictured in FIG. 1 and the previously described method, thereby ensuring the consistency of the final product. An analysis system 56 can be installed to determine if the distribution of the rubber particles within the final product is acceptable. This analysis may be done in many ways, including comparing an optimal reference chromatogram with the produced chromatogram 32. In response to this analysis, the analysis system 56 can regulated the flow of rubber particles to the blending system 52 by signaling the input control system 54, which can make the appropriate adjustments in the flow of material to the blending system 52.

It should be realized by one of ordinary skill in the art that the invention is not limited to the exact construction or method illustrated above, but that various changes and modifications may be made without departing from the spirit and scope of the invention as described within the following claims.

What is claimed is:

1. In a method for producing a water insoluble matrix containing a desired size distribution of a non continuous phase material of the type where a quantity of a monomer material and a quantity of a non continuous phase material are added through control means to a polymerization system, then mixed, polymerized, and finally extruded, the improvement consisting of:
    removing a sample from the system after initial mixing but before the polymerization is complete;
    determining the distribution according to size of the sample by nonaqueous hydrodynamic chromatography, which includes the steps of:
    a. placing the sample in a solvent effective for dissolving the matrix thereby forming a mixture of the particles dispersed in a solution comprising the solvent and the matrix;
    b. adding a controlled amount of the mixture to an essentially nonaqueous carrier liquid;
    c. eluting the carrier liquid containing the mixture through a separating medium effective for sorting the particles according to size wherein the largest particles are eluted first and the smallest particles are eluted last;
    d. monitoring the effluent from the separating medium by measuring and recording a signal representing a physical property of the effluent that is responsive to the concentration of particles in the effluent;
    comparing the results from the nonaqueous hydrodynamic chromatography analysis to the desired size distribution;
    making adjustments in the control means and/or the supply of the non continuous phase material in order to make the polymerized product more closely resemble the desired product.
2. The method of claim 1 further comprising the step of adding a dimension fixing material effective for inhibiting the particles from contracting or expanding upon the dissolving of the matrix.
3. The method of claim 2 wherein the dimension fixing material is osmium tetroxide.
4. The method of claim 1 wherein the solvent which dissolves the matrix is substantially similar to the carrier liquid.
5. The method of claim 4 wherein the solvent which dissolves the matrix and the carrier liquid are both dimethylformamide.
6. The method of claim 1 wherein the matrix containing the particles is a polymeric substance.
7. The method of claim 6 wherein the polymeric substance is polystyrene.
8. The method of claim 6 wherein the polymeric substance is acrylonitrile-styrene copolymer.
9. The method of claim 1 wherein the matrix containing the particles is partially polymerized.
10. The method of claim 1 wherein the particles are polybutadiene.
11. The method of claim 1 wherein the diameters of the particles are in the range of from about 0.1 micrometers to about 1 micrometer.
12. The method of claim 1 wherein the separating medium is a chromatography column packed with highly cross-linked styrene divinylbenzene (S/DVB) polymer.
13. The method of claim 12 wherein the S/DVB polymer has a diameter of about 20 micrometers.
14. The method of claim 1 wherein the measured signal is turbidity.

* * * * *